United States Patent [19]

Aoki et al.

[11] 4,426,454

[45] Jan. 17, 1984

[54] DIAGNOSTIC METHOD FOR IMMUNE DISORDERS

[75] Inventors: Tadao Aoki; Hideo Miyakoshi, both of Niigata; Mikio Mizukoshi, Saitama, all of Japan

[73] Assignee: Fujirebio Kabushiki Kaisha, Tokyo, Japan

[21] Appl. No.: 246,544

[22] Filed: Mar. 23, 1981

[30] Foreign Application Priority Data

Mar. 26, 1980 [JP] Japan .................................. 55-37504

[51] Int. Cl.$^3$ ....................... G01N 33/58; G01T 1/00; C12Q 1/29
[52] U.S. Cl. .................................... 436/504; 435/29; 436/501; 436/503
[58] Field of Search ............................. 424/1, 1.5, 12; 23/230 B; 435/29; 436/501, 503, 504

[56] References Cited

U.S. PATENT DOCUMENTS 3,991,182 11/1976 Spitler et al. ........................ 424/101
4,182,751 1/1980 Ayme .................................. 424/92

OTHER PUBLICATIONS

Forsgren et al, Eur. J. Immunol., 6:207–213 (1976).
Gausset et al, Immunol., 41:891–897 (1980).
Williams et al, Proc. Soc. Exp. Biol. Med., 139:480–483 (1972).
Tsuyoshi Sakane et al, J. Imminol., 120:302–311 (1978).
Rodey et al, J, Immunol., 108:178–182 (1972).
Shayegani et al, "Specific and Nonspecific Cel-l-Mediated Resistance to Influenza Virus in Mice", Infection and Immunity, Jun. 1974, pp. 991–984.
Mudd et al, "Delayed-Type Hypersensitivity to Staphylococcus aureus in Human Subjects", Journal of the Reticuloendothelial Society, vol. 8, No. 5., Nov. 1970.
Oeding, "Serological Typing of Staphylococci", The Gade Institute, Dept. of Bacteriology, University of Bergen, Norway).
Dean et al, "Functional Activities of Rosette Separated Human Peripheral Blood Leukocytes", The Journal of Immunology, vol. 115, No. 5, Nov. 1975.
Mudd, Delayed-Type Hypersensitivity to S. Aureus and Its Uses.
Allen et al, "Protection of Mice Against Vaccinia Virus by Bacterial Infection and Sustained Stimulation with Specific Bacterial Antigens", Infection and Immunity, Jan. 1973, pp. 62–67.
Baker, "Treatment of Chronic Bronchial Asthma", American Practitioner and Digest of Treatment, vol. 9, No. 1, Apr. 1958, pp. 591–598.
Dean et al, "In Vitro Human Reactivity to Staphylococcal Phage Lysate", The Journal of Immunology, vol. 115, No. 4, Oct. 1975, pp. 1060–1064.

Primary Examiner—Christine M. Nucker
Attorney, Agent, or Firm—Flynn, Thiel, Boutell & Tanis

[57] ABSTRACT

A diagnostic method for immune disorders comprising determining the immunoglobulin production or the DNA (deoxyribonucleic acid) synthesis of peripheral blood lymphocytes by stimulation with a new mitogen derived from either disintegrated microorganisms or culture fluid of microorganisms belonging to Staphylococcus.

12 Claims, No Drawings

DIAGNOSTIC METHOD FOR IMMUNE DISORDERS

DESCRIPTION OF THE INVENTION

The present invention relates to a diagnostic method for a variety of diseases accompanied by immune disorders of the human body. Hereinafter, such diseases are referred to as "immune disorders". Particularly, this invention relates to a diagnostic method for immune disorders comprising determining the immunoglobulin production and the DNA synthesis of peripheral blood lymphocytes (PBL) stimulated by disintegrated cells or the culture fluid of microorganisms belonging to Staphylococcus.

There are two kinds of cells relating to the immunity of human body; one, bone marrow-derived lymphocytes (B cells) which produce immunoglobulins, and the other, thymus-derived lymphocytes (T cells) which relate to cell-mediated immunity. This invention relates to diagnosis of disease accompanied by the functional disorder of B cells. In order to detect this disorder, the amount of immunoglobulin produced by these cells is determined after stimulation with a mitogen. It is also well known that B cells of patients with immune disorders produce less immunoglobulin than those of healthy persons. Therefore, as lymphocyte stimulating substances (mitogens), Protein A, purified protein derivatives of *Mycobacterium tuberculosis* (PPD), bacterial cells of Staphylococcus, and lipopolysaccharide (LPS) have been proposed for this purpose. Although Protein A does not induce the immunoglobulin G production of peripheral B cells, PPD stimulates such production depending on the degree of infection with *Mycobacterium tuberculosis*. On the other hand, *Staphylococcus aureus* and LPS do not exhibit a sufficient stimulating effect on B cells. Because of these disadvantages, the above-mentioned mitogens are not suitable for practical use. Thus, the method of present invention has been developed to determine exactly the amount of Immunoglobulin G production by use of a new mitogen.

We have invented this method on the basis of a finding that disintegrated *Staphylococcus aureus* and/or the culture fluid thereof act as mitogens for this purpose. Any strain of *Staphylococcus aureus* can be used in this invention. The components obtained by either disintegrating the bacterial cells or obtaining the culture fluid of such cells have excellent stimulating effects on B cells. The fractions obtained at various steps of purification may be used for this purpose.

PREFERRED EMBODIMENTS

Samples 1, 2 and 3 for use in the method of the present invention were prepared as follows:

Sample 1: *Staphylococcus aureus* (S 11 Strain) was cultured on an agar plate (Bactoagar, Difco) for 16 hours and then in beef heart infusion broth at 30° C. for 16 hours, obtaining about $10^9$/ml of colony forming units of bacteria. To this broth was added polyvalent staphylococcus bacteriophage (B 985 Strain), and the mixture was incubated at 30° C. for 16 hours to disintegrate (lyse) the bacteria, and then filtered to remove debris. The filtrate (lysate) was used as Sample 1.

Sample 2: *Staphylococcus aureus* (S 33 Strain) was cultured in the same way as for the culture of Sample 1. The broth containing the bacteria was subjected to ultrasonic oscillation at 9 KHz/sec for one minute to lyse the bacteria and then filtered to remove debris. The filtrate (lysate) was used as Sample 2.

Sample 3: *Staphylococcus aureus* (18 Z Strain) was cultured in the same way as that of Sample 1. The broth containing *Staphylococcus aureus* was centrifuged at 60,000 XG for 3 hours, and then the supernatant was filtered. The filtrate was used as Sample 3.

Comparison tests were carried out as follows: PBL from healthy persons and patients with immune disorders were cultured with the individual samples. Each of Samples 1, 2 and 3 was added to each sample of PBL suspension, and these mixtures were incubated at 37° C. for 168 hours. Amounts of immunoglobulin (IgM and IgG) produced were measured by the microtiter solid-phase radioimmunoassay method. The results are summarized in Table 1.

TABLE 1

| Sample No. | Concentration of immunoglobulin (ng/ml±S.E.)* | | | |
|---|---|---|---|---|
| | Healthy donors | | Patient with immune disorders | |
| | IgM | IgG | IgM | IgG |
| 1 | 1,517±190 | 1,935±358 | 428±39 | 521±55 |
| 2 | 918±116 | 1,535±456 | 319±30 | 301±27 |
| 3 | 2,110±268 | 1,463±168 | 536±48 | 369±34 |

*S.E. Standard Error

The immunoglobulin production of PBL from the patients with immune disorders was reduced to $\frac{1}{3}$ to $\frac{1}{4}$ in comparison with that of healthy persons' PBL. Similarly, the DNA (deoxyribonucleic acid) synthesis of PBL was compared between healthy persons and patients with immune disorders. Incorporation of tritium thymidine ($^3$H-TdR) was determined with a liquid scintillation counter (Table 2). The DNA synthesis of PBL from the patients with immune disorders was reduced to $\frac{1}{2}$ to $\frac{1}{3}$ in comparison with that of healthy persons' PBL. In conclusion, the diagnosis of patients with immune disorders can be achieved by stimulating PBL with mitogens, i.e., a lysate of *Staphylococcus aureus* or a filtrate of the culture fluid of *Staphylococcus aureus*, in order to measure the capacities for immunoglobulin production and DNA synthesis of the peripheral blood lymphocytes.

TABLE 2

| Sample No. | Incorporation of $^3$H-TdR (cpm±S.E.) | |
|---|---|---|
| | Healthy donors | Patient with immune disorders |
| 1 | 11,956±483 | 4,675±231 |
| 2 | 6,374±251 | 2,180±112 |
| 3 | 12,311±282 | 5,156±389 |

What is claimed is:

1. A method for diagnosing, in a human being undergoing testing, the existence of an immune disorder of the type in which the peripheral blood lymphocytes of the human being produce a substantially lower amount of immunoglobulins than the peripheral blood lymphocytes of a normal healthy human being, comprising the steps of: culturing a sample of peripheral blood lymphocytes taken from the human being undergoing testing with a mitogenic substance selected from the group consisting of (1) a lysate prepared by sonic destruction of *Staphylococcus aureus* cells and (2) the soluble growth products of the metabolic activity of *Staphylococcus aureus* cells, under conditions effective to induce production of immunoglobulins or to produce DNA; then measuring either the amount of immunoglobulin or the amount of DNA in the sample; then comparing the measured value of immunoglobulin concentration or DNA in the sample with the corresponding value obtained when the peripheral blood lymphocytes of a normal healthy human being are tested in the same way, a low value of immunoglobulin or DNA production for the sample relative to the corresponding value for a normal healthy human being indicating the presence of an immune disorder in the human being undergoing testing.

2. A method according to claim 1, wherein said amount of immunoglobulin in said sample is measured.

3. A method according to claim 1, wherein said amount of DNA in said sample is measured.

4. A method according to claim 2, wherein the concentration of IgM and IgG in said sample are measured.

5. A method according to claim 1, wherein said low value of immunoglobulin production for said sample is a concentration in the range of $\frac{1}{3}$ to $\frac{1}{4}$ lower than said corresponding value for a normal healthy human being.

6. A method according to claim 1, wherein said low value of DNA production for said sample is $\frac{1}{2}$ to $\frac{1}{3}$ lower than said corresponding value for a normal healthy human being.

7. A method as claimed in claim 1, wherein said amount of DNA in the sample is measured by tritium thymidine incorporation.

8. A method according to claim 1, further comprising a step of subjecting cells of *Staphylococcus aureus* to ultrasonic oscillation at at least 9 KHz/seconds to obtain said lysate, said mitogenic substance consisting essentially of said lysate.

9. A method according to claim 1, further comprising the steps of culturing *Staphylococcus aureus* cells on a nutritive culture medium for a period of time sufficient to obtain a colony of said cells, and then centrifuging said cells and culture medium to obtain a supernatant, which supernatant is used as solid mitogenic substance containing soluble growth products of the metabolic activity of said *Staphylococcus aureus* cells.

10. A method as claimed in claim 9, wherein said colony consists of at least approximately $10^9$/ml units of said cells, further comprising a step of filtering said supernatant to produce a filtrate which is used as said mitogenic substance.

11. A method according to claim 1, wherein said peripheral blood lymphocytes are B-cells.

12. A method for diagnosing, in a human being undergoing testing, the existence of an immune disorder of the type in which the peripheral blood lymphocytes of the human being produce a substantially lower amount of immunoglobulins than the peripheral blood lymphocytes of a normal healthy human being, comprising the steps of: culturing a sample of peripheral blood lymphocytes taken from the human being undergoing testing with a mitogenic substance consisting essentially of a lysate prepared by sonic destruction of *Staphylococcus aureus* cells, under conditions effective to induce production of immunoglobulins or to produce DNA; then measuring either the amount of immunoglobulin or the amount of DNA in the sample; then comparing the measured value of immunoglobulin concentration or DNA in the sample with the corresponding value obtained when the peripheral blood lymphocytes of a normal healthy human being are tested in the same way, a low value of immunoglobulin or DNA production for the sample relative to the corresponding value for a normal healthy human being indicating the presence of an immune disorder in the human being undergoing testing.

* * * * *

UNITED STATES PATENT AND TRADEMARK OFFICE
CERTIFICATE OF CORRECTION

PATENT NO. : 4 426 454

DATED : January 17, 1984

INVENTOR(S) : Tadao Aoki et al

It is certified that error appears in the above-identified patent and that said Letters Patent is hereby corrected as shown below:

Column 4, line 1; change "solid" to ---said---.

Signed and Sealed this

Eighth Day of May 1984

[SEAL]

Attest:

Attesting Officer

GERALD J. MOSSINGHOFF

Commissioner of Patents and Trademarks